United States Patent [19]

Kondo et al.

[11] Patent Number: 4,897,224
[45] Date of Patent: Jan. 30, 1990

[54] METHOD FOR PRODUCING FERULYL STANOL DERIVATIVES

[75] Inventors: Yoshikazu Kondo, Sendai; Shuetu Suzuki; Morio Kuboyama, both of Tokyo, all of Japan

[73] Assignee: Morinaga Milk Industry Co., Ltd., Tokyo, Japan

[21] Appl. No.: 831,853

[22] Filed: Feb. 24, 1986

[30] Foreign Application Priority Data

| Mar. 5, 1985 [JP] | Japan | 60-41932 |
| Mar. 7, 1985 [JP] | Japan | 60-43725 |
| Mar. 7, 1985 [JP] | Japan | 60-43726 |
| Mar. 9, 1985 [JP] | Japan | 60-45732 |

[51] Int. Cl.$^4$ .............................................. C07J 9/00
[52] U.S. Cl. ................................................. 260/397.2
[58] Field of Search ............................. 514/170, 182; 260/397.2, 397.25

[56] References Cited
PUBLICATIONS

Chemical Abstracts, vol. 106 (1987); #84952E; Kondo et al.
Chemical Abstracts, vol. 106 (1987); #96971y; Kondo et al.

*Primary Examiner*—Douglas W. Robinson
*Assistant Examiner*—Joseph A. Lipovsky
*Attorney, Agent, or Firm*—Oblon, Spivak, McClelland, Maier & Neustadt

[57] ABSTRACT

A fertility drug is made from an effective component comprising ferulyl stanol derivative represented by the following formula (I) and/or phytosterol fatty acid ester represented by the following formula (II). Such an effective component may be extracted from Job's tears seed, preferably bran thereof. A synthetic method of producing ferulyl phytostanol derivative is also disclosed.

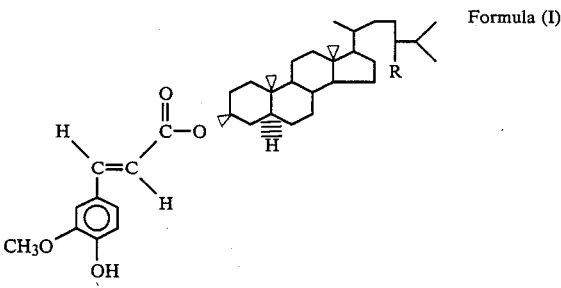

Formula (I)

(R: —CH$_3$ or —C$_2$H$_5$)

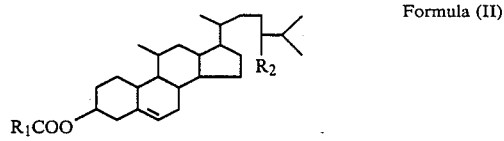

Formula (II)

2 Claims, 4 Drawing Sheets

METHOD FOR PRODUCING FERULYL STANOL DERIVATIVES

BACKGROUND OF THE INVENTION

1. Field of the Invention

The present invention relates to a fertility drug or an ovulation-inducing drug and a method of producing the same, and more particularly to a fertility drug having an effective component comprising a composition or compositions involved in Coix lacryma-jobi var. mayuem Stapf L. (hereinlater described simply as "Job's tears") which is extracted from Job's tears or synthetically produced in organic reactions.

2. Prior Art Description

Typically known to the world as fertility drugs are those comprising clomiphene and cyclohexil. These conventional fertility drugs have been used for more than 20 years and their pharmacological effects are recognized in clinical trials. However, it has been found in practice that they will often cause extraordinary sex periods, resulting in such troubles as multiple pregnancy and failure of pregnancy. They often produce side effects. Under the circumstances, nevertheless, no other fertility drugs have yet become available for practical purposes.

Examination and study on novel fertility drugs have been attempted. For example, it has been found that leaves of corn, rye and wheat contain a material which will induce ovulation of domestic rabbits (Niigata Medical Society Bulletin; vol. 78, page 305; in 1964; Japan). Up to the present, however, its ovulation-inducing effect on human-kind has not yet been proved and therefore such a material is still not applicable to practical use.

Meanwhile, it has become apparent that some pharmacological effects will inhere in extractants from Job's tears and coix seed, a fruit of Job's tears prepared by removing hulls and peels from Job's tears seed. "Seiyakugaku" by Inagaki et al; published by Nankodo in 1975 in Japan; page 162; writes as follows:

(1) The extractants of Job's tears and coix seed have diuretic effects and therefore may be used for the remedy of tumor, beriberi, nephrolith and cystolith and harumph.

(2) They may be used as painkillers and crampkillers.

(3) They are good for warts and roughness.

Moreover, it has now been confirmed that proteins extracted from unthreshed powder of Job's tears seed will spur secretion of human milk (Masahiko Shigemitsu; Bulletin of Kumamoto Local Department of Japan Women Science Society; vol. 3, page 191; 1944). An anticancer material can be isolated from coix seed (Chemical and Pharmaceutical Bulletin, Japan; vol. 9, page 43,; 1961). However, the ovulation-inducing effect of Job's tears and/or the extractants thereof has not yet been known in the prior art.

SUMMARY OF THE INVENTION

It is therefore an object of the invention to provide a novel fertility drug of a type different from the conventional one typically comprising clomiphene and cyclohexyl, capable of inducing ovulation in physiologically natural manner, without causing abnormal sex periods.

Another object of the invention is to provide a novel method of synthetically producing an ovulation-inducing material, identical to that contained in Job's tears, with high efficiency, to thereby make it possible to manufacture on commercial basis a fertility drug having said ovulation-inducing material as an effective component.

According to an aspect of the invention there is provided a fertility drug having an effective component comprising oil-soluble fraction of a whole or a part of Job's tears seed.

According to another aspect of the invention there is provided a fertility drug having an effective component comprising ferulyl stanol derivative and/or phytosterol fatty acid ester, contained in Job's tears. The said fertility drug is prepared by incorporating ethyl acetate into Job's tears bran to extract an oil-and-fat fraction from the Job's tears bran and collecting the effective component contained in the oil-and-fat fraction.

According to still another aspect of the invention there is provided a synthetic method of producing ferulyl phytostanol derivative comprising the steps of acetylating ferulic acid with a mixture of pyridine and acetic anhydride, treating the acetylated ferulic acid with thionyl chloride to prepare and acid chloride, reacting in the presence of pyridine the acid chloride with phytostanol to form a phytostanol compound, dissolving the phytostanol compound into a mixture of methanol and chloroform, and adding sodium borohydride to a resulting solution, with stirring, to thereby deacetylate the phytostanol compound.

BRIEF DESCRIPTION OF THE DRAWINGS

Further objects and advantages of the present invention can be fully understood from the following detailed description when read in conjunction with the accompanying drawings, in which.

DETAILED DESCRIPTION OF THE INVENTION

The present invention according to one aspect thereof is concerned with a fertility drug or an ovulation-inducing drug having an effective component comprising an oil-soluble fraction of a whole or a part of Job's tears seed. The oil-soluble fraction may be extracted from powder which is prepared by grinding the whole of the Job's tears seed. Alternatively, the Job's tears seed is threshed and purified in a known manner to be classified into coix seed, bran and hulls, from any of which may be extracted the oil-soluble fraction. In view of extractability, however, the use of bran itself or the whole seed, inclusive of the bran, is preferred.

In extraction of the oil-soluble fraction from Job's tears seed, an extracting solvent may be n-hexane, ethyl acetate ester or any other suitable one. In the case of n-hexane being used, yield of the oil-soluble fraction would be decreased but it is easier to be evaporated after extraction, so that n-hexane is a preferred solvent in a practical sence.

The fertility drug thus prepared has an effective component of the oil-soluble fraction extracted from Job's tears seed or a purified one thereof. A vehicle, matching agent, diluent and any other kind of additives may be incorporated alone or in combination, upon demand. The fertility drug may be in the form of pellets, powder medicines, capsules, syrup or injections, and applied orally or externally.

For better understanding of the invention some exemplifying tests will be given hereunder.

Test 1

In this test, a water-soluble fraction and an oil-soluble fraction were extracted respectively from the whole seed of Job's tears and the ovulation-induce effects of the respective fractions were measured and compared to each other.

Figure 1:
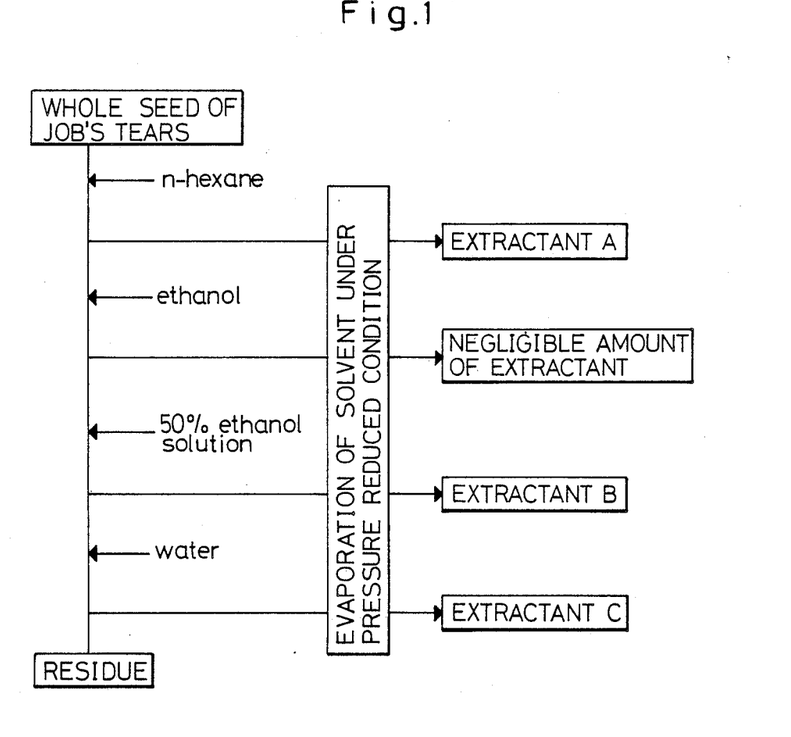
FIG. 1 diagrammatically illustrates the steps of the test method in Test 1 for extracting components from a whole seed of Job's tears with extracting reagents of n-hexane, ethanol, 50% ethanol solution and water.

The whole seed of Job's tears was ground into powder to prepare 500 g sample. This sample powder was subjected to extraction with an extracting reagent of 1.5 l n-hexane at a temperature range of 15°~20° C. After the extraction the extracting reagent was distilled under pressure reduced conditions to obtain about 45 g of yellow, oily substance (extractability of about 9% by weight—the percentage is given by weight throughout the Specification unless otherwise specified). This yellow, oily extractant was determined as component A. Then the residue after extraction of component A was further subjected to extraction with 1.5 ethanol but only a negligible amount of an extractant was obtained. The residue was dipped into a leaching liquid of 50% ethanol solution, and the leaching liquid was concentrated at a temperature below 40° C. under pressure reduced conditions, to thereby obtain a precipitate and about 2 g extractant. This extractant was determined as component B. Then, from the residue after extraction of component B was extracted with 1.5 l water, a small amount of another extractant, which was determined as component C. In summary, components A, B and C were extracted in such manner as diagrammatically illustrated in FIG. 1.

These components A, B and C were qualitatively analized in a known manner to find that component A contains glyceride and such esters as ferulic acid ester, component B contains polyamido and component C contains amino acid and peptide.

Next, the ovulation-inducing effect or activity of the respective components A, B and C were tested in the following manner. More particularly, 70 golden hamsters in the age of 5~8 weeks were devided into 7 groups each having 10 golden hamsters. The fodder were prepared by adding to the basic fodder 1% of components A, B and C, and given orally to the group Nos. 1, 2 and 3, respectively. As the average intake of the fodder of a golden hamster in 19 g a day, 190 mg of the respective components were given in the respective groups. They were fed with such fodder for 3 weeks and then slaughtered. The group Nos. 4, 5 and 6 were fed in the same manner, but after 3 weeks' feed of the fodder containing the components only the basic fodder were given thereto for 5 weeks and then slaughtered. Whereas, the group No. 7 was initially given only the basic fodder for 3 weeks and then slaughtered.

As to the respective groups, the sex periods were observed and the number of naturally produced ova was counted before they were slaughtered, and after slaughtered the weight and the state of the ovary were observed by means of dissection. The results of these tests are shown in the following Table I.

TABLE I

| test sample | | comparison of sex period | | number of natural ovulation | dissection test | |
|---|---|---|---|---|---|---|
| group No. | component added | sex period | remarks | | weight of ovary (mg) | state of ovary |
| 1 | A | 4 days | regular | 17 ± 2 ※ | 19.48 ± 2.35 | (++) |
| 2 | B | 4 days | regular | 12 ± 2 | 18.01 ± 0.34 | (±) |
| 3 | C | 4 days | regular | 12 ± 2 | 17.93 ± 0.23 | (±) |
| 4 | A | 4 days | regular | 17 ± 3 ※ | 19.59 ± 0.23 | (++) |
| 5 | B | 4 days | regular | 12 ± 2 | 18.20 ± 0.26 | (+) |
| 6 | C | 4 days | regular | 12 ± 2 | 17.83 ± 0.56 | (±) |
| 7 | — | 4 days | regular | 12 ± 2 | 18.03 ± 0.15 | (±) |

Notes:
① Figures in column of Sex Period show the average.
② In the column of State of Ovary the marks (±), (+) and (++) mean relative comprison in the number of corpora lutea found in cut-outs of the ovary.
③ the mark ※ identified in the column Natural Ovulation means that there could be found a significance with respect to other groups at a significance level of 1%.

As it appears from the results shown in Table I, the component A extracted from the whole seed of Job's tears with n-hexane will promote natural ovulation without disturbing the sex periods. As a result of organic dissection, the effective component contained in the component A was proved to act on the sex center so as to promote formation of corpora lutea.

Meanwhile, Table I also shows that this effective component is contained only in the oil-soluble fraction of the Job's tears seed and is scarely present in the extractants obtained with ethanol, 50% ethanol solution and water.

Test 2

This test was carried out to find the optimal dosage of the ovulation-inducing effective component contained in the component A extracted in Test 1.

First, the component A was dipped into leaching liquids of ethanol, 50% ethanol solution and water, step by step, and then the leaching liquid were removed. Then the residue was purified by column chromatography with h-hexane. Thus, a purified extractant was obtained in a yield of 90% of the component A.

Figure 2:
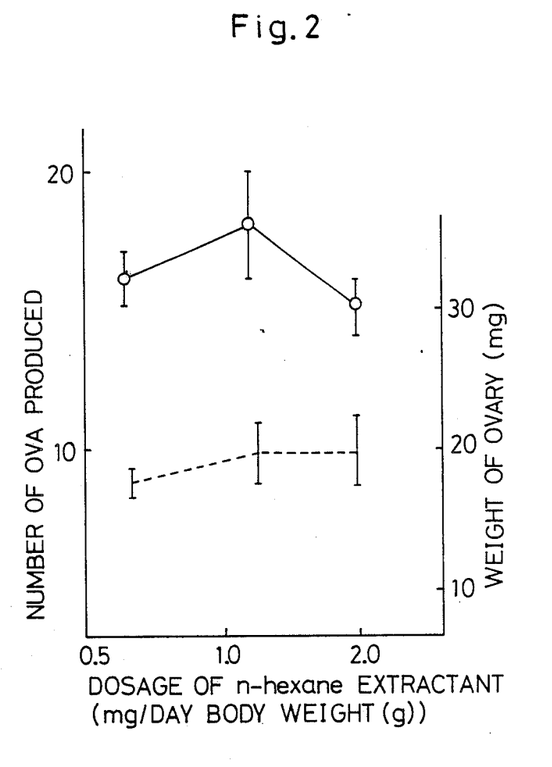
FIG. 2 is a graph showing relationship between dosage of a purified extractant obtained from Job's tears seed with n-hexane and the number of naturally produced ova and the state of ovaria.

This extractant was dissolved in 0.2 ml soybean oil in quantities varied between 95~380 mg to prepare three fodder containing different quantities of the extractant, which were orally applied by injector to three groups each having 10 golden hamsters, once a day, for 3 weeks. Thereafter, the test animals were slaughtered. These groups were put into the tests for the natural ovulation and the ovary weight in the same manner as in Test 1, upon which matural relation of the dosage of the extractant per body weight of a golden hamster was determined with these parameters. The test results are shown in FIG. 2.

As shown, the optimal dosage per body weight of a golden hamster was found to be in a range of 0.76~1.4 mg/g a day. Accordingly, provided the body weight of a grownup is 60 kg, 4.6~8.4 g/day of the purified n-hexane extractant was determined to be an optimal range when applied to an adult. The medication term will be dependent upon the condition of a patient and varied case by case.

Test 3

In this test, extractability of the effective component obtained respectively from the whole seed, coix seed, bran and hull of Job's tears was measured and compared to each other.

Respective 500 g powder were prepared by grinding the coix seed, bran and hull of Job's tears seed, and extractants corresponding to component A were extracted in the same manner as in Test 1. Quantities of the extractants thus obtained and extractability in the respective cases are shown below in Table II. Data for the whole seed in Table II are the reproduction of those in Table I. It will be obvious from Table II that the greatest extractability was gained in the case of bran, leading to the fact that the effective component is in substance contained in the bran of Job's tears seed. Thus, the effective component can be extracted with great efficiency from the bran alone or the whole seed including the bran.

TABLE II

| test sample | amount of extractant (g) | extractability (%) |
|---|---|---|
| whole seed | 45.0 | 9.0 |
| coix seed | 27.0 | 5.4 |
| bran | 80.0 | 16.0 |
| hull | 0.6 | 0.12 |

Note:
The extractability is calculated by the equation of amount extractant (g)/ sample powder (500 g) × 100

The inventors have made thorough investigation of the effective ovulation-inducing material contained in Job's tears seed and found in the end that ferulyl stanol derivatives expressed by the following formula (I) and/or phytosterol fatty acid ester expressed by the following formula (II) has significant effect and activity on induction of natural ovulation. Based on this fact the inventors have come to a successful end that a novel fertility drug having an effective component comprising ferulyl stanol derivatives and/or phytosterol fatty acid ester may be prepared.

Formula (I)

(R: —CH$_3$ or —C$_2$H$_5$)

Formula (II)

(R$_1$: remaining radical of palmitic or stearic acid  R$_2$: —CH$_3$ or —C$_2$H$_5$)

Stanol ferulic acid derivatives represented by the formula (I) may be, for example, trans-ferulyl stigmastanol, trans-ferulyl campestanol or a mixture thereof.

Phytosterol fatty acid ester represented by the formula (II) may be, for example, β-sitosterol palmitic acid ester, β-sitosterol stearic acid ester, campesterol palmitic acid ester, campesterol stearic acid ester or any one of the combinations thereof.

A process for producing the above fertility drug is described in detail hereunder.

First, a Job's tears seed is threshed and purified in a known manner to be separated into coix seed, bran and hull. To 1 part of the bran is incorporated 3~5 parts (by weight; the part is given by weight throughout the Specification unless otherwise specified) of ethyl acetate, and the resultant is agitated at 15°~20° C. for 5~10 hours, thereby extracting an oil-and-fat fraction. The extract is then filtered to remove an insoluble fraction.

To 1 part of the residue is incorporated 3~5 parts of ethanol, and the solution is agitated at 15°~20° C. for 5~10 hours. The resultant extract is then filtered to remove an insoluble fraction. The ethanol-soluble fraction thus obtained is distilled to remove ethanol, thereby obtaining an ethanol extractant. To 1 part of the ethanol extractant is added 3~5 parts of ethyl acetate, and the solution is agitated at 15°~20° C. for 5~10 hours, to obtain an ethyl acetate-soluble fraction.

The oil-and-fat fraction and the ethyl acetate-soluble fraction are mixed together and ethyl acetate is separated from the mixture. The resultant is supplied to a column charged with silica gel to effect gradient elution with a mixed eluent of n-hexane and ethyl acetate, whereby fractions eluted with the mixed eluents of n-hexane and ethyl acetate having mixing ratios of 30:1~10:1 and/or 100:05~100:1 are collected. The fractions thus collected are mixed together and the eluents are removed from the mixture, thereby obtaining ovulation-induceing materials. The fractions eluted with the eluent of 30:1~10:1 mixture of n-hexane and ethyl acetate will contain ferulyl stanol derivatives and the fractions eluted with the eluent having the mixing ratio of 100:05~100:1 will contain phytosterol fatty acid ester. Effective materials will be contained in the respective eluates obtained with the eluents having different ranges of mixing ratio and may be used alone or in a mixed state to manufacture the fertility drug according to the invention. The drug may be a pellet, a powder medicine, a capsule, an injection or in any other form, and applied orally or externally. The dosage of the drug will vary depending upon the condition of a patient and the way of application, but in most cases 40~80 mg once a day will be effective when orally applied to an adult.

The fertility drug of the invention having an effective component comprising ferulyl stanol derivative and/or phytosterol fatty acid ester will be further described by way of exemplifying tests.

Test 4

This test was carried out to observe physical and chemical characteristics of ferulyl stanol derivative. The test sample was X component prepared in the same manner as in Example 3, described later.

This test sample was analized by thin-layer chromatography to detect a single spot (hereinlater defined as material X) which manifested a blue-green color with sulfuric acid and was distinguishable in ultraviolet rays.

Figure 3:
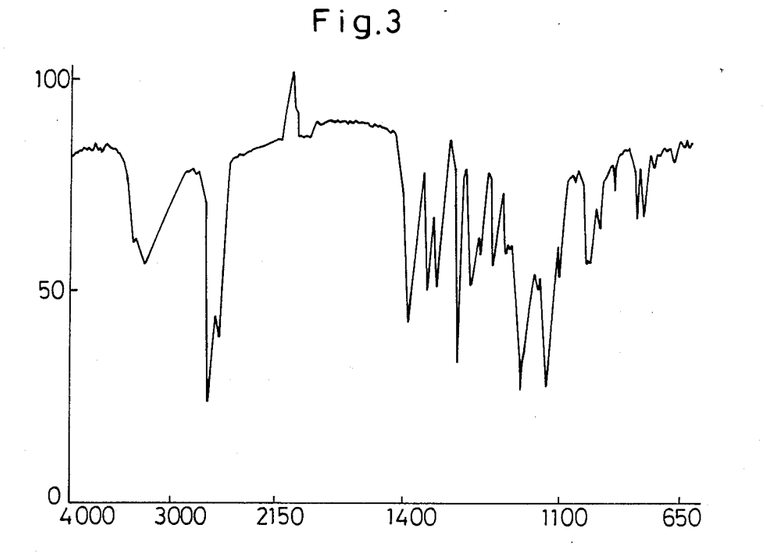
FIGS. 3 and 4 are charts showing infra-red spectrum and nuclear magnetic resonance spectrum of a fertility drug according to one aspect of the invention.
Figure 4:
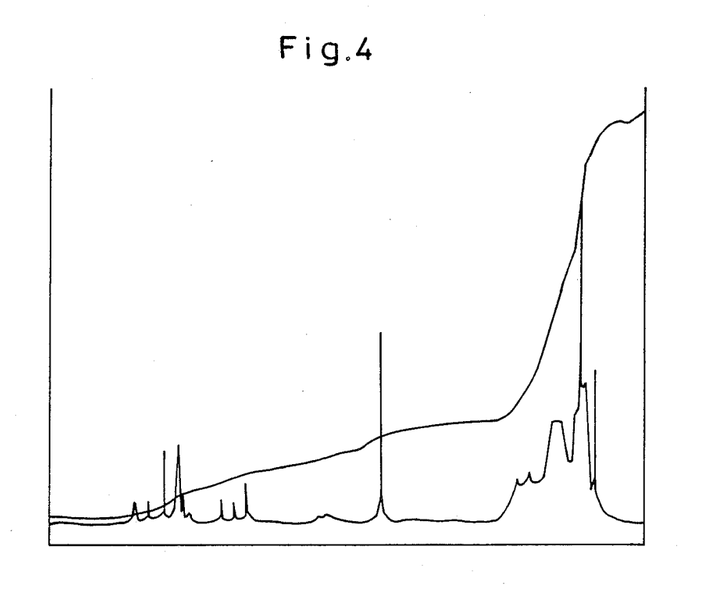

The material X was purified by alumina column chromatography and isolated as colorless, needle-like crystals having melting point of 156° C. The material X showed positive adsorpotion in the Gibbs' adsorpotion test and had a M+ peak at m/e 592 in the mass spectrometry. In the infra-red spectrophotometry, as shown in FIG. 3, it showed adsorption signals based on hydroxyl group at $3120\sim3500$ cm$^{-1}$, conjugated carboxyl group at 1710 cm$^{-1}$, double-bond of $\alpha,\beta$-unsaturated carbonyl group at 1640 cm$^{-1}$, C-C stretching vibration of benzene ring at 1600 and 1510 cm$^{-1}$, and out-of-plane deformation vibration of benzene ring at 840 cm$^{-1}$, respectively. In the nuclear magnetic resonance spectrometry (CDCl$_3$), as shown by the chart of FIG. 4, it manifested a signal pattern peculiar to phytosterol at 0.62~2.0 ppm. Further, signals were found based on methoxy group at 3.88 ppm, and the AB type spin-spin-coupling (J=16 Hz) of hydrogen in the double-bond of $\alpha,\beta$-unsaturated carbonyl group of cinnamic acid derivative and the ABM type spin-spincoupling of hydrogen in the tri-substituted benzene ring thereof was found at 6.22 ppm and 7.55 ppm, respectively. The singlet of 1H at 5.95 ppm was disappeared by adding D$_2$O. According to these results, the material X was determined to have hydroxyl group of a phenol.

The material X was subjected to alkalic hydrolysis to be separated into an acid and a neutral fractions, to both of which were applied chemical analysis to prove that only ferulic acid was isolated from the acid fraction (which was identified in comparison with specimen). The neutral fraction was silylated in a known manner and then quantitatively analyzed by gas chromatography, whereby it was identified as a mixture of stigmastanol and campestanol in a ratio of 9:1.

Further, the material X was acetylated with a mixture of pyridine and acetic acid to form mono-acetal in the form of colorless, platy crystals, having melting point of 155°~156° C. According to nuclear magnetic resonance spectrometry (CDCl$_3$), there could be seen signals based on methyl and methylene radicals of phytosterol at 0.6~2.0 ppm, and a signal based on acetyl group at 2.32 ppm. At 3.84 ppm, a signal of singlet of 3H was found based on methyl of methoxy group. The AB type spin-spincoupling of olefin hydrogen in $\alpha,\beta$-unsaturated carboxyl group was noted at 6.32 ppm and 7.60 ppm, and the ABM type spin-spincoupling of hydrogen on the tri-substituted benzene ring appeared at 7.07 ppm.

Consequently, the material X was identified as a mixture of trans-ferulyl stigmastanol and trans-ferulyl campestanol in a ratio of 9:1. By the results of analyses including its melting point, the trans-ferulyl stigmastanol was found to be the same material as dihydro-$\beta$-sitosterol ferulic acid ester which is isolated from a corn embryo bud oil (Tamura et al; "Nippon Kagaku Zasshi (Japan Chemical Magazine)"; vol. 79, page 1011; in 1958).

Test 5

This test was carried out to reveal physical and chemical characteristics of phytosterol fatty acid ester. Y components, prepared in the same manner as in Example 3, described later, was used as a test sample.

Figure 5:
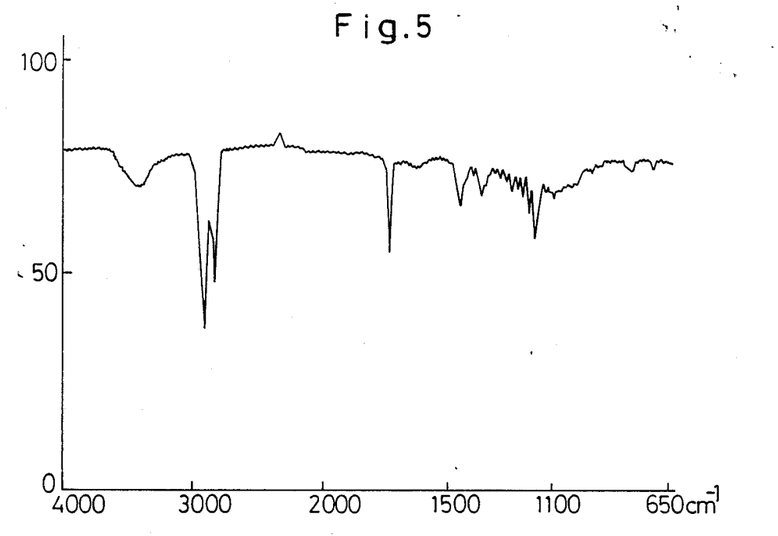
FIGS. 5 and 6 are charts showing infra-red spectrum and nuclear mabnetic resonance spectrum of a fertility drug according to another aspect of the invention.
Figure 6:
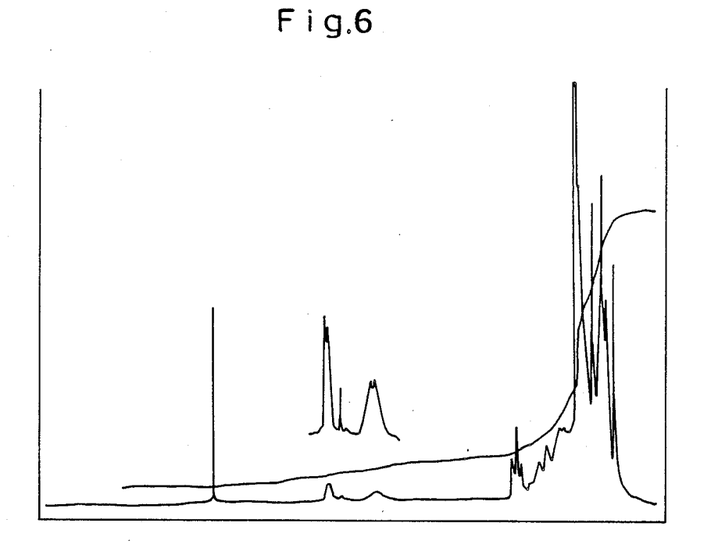

This sample was analized by thin-layer chromatography in a known manner to isolate a material of colorless, needle-like crystals, having a melting point of 64°~65° C., which showed a spot manifesting a blue-green color with sulfuric acid and being distinguishable in ultraviolet rays. According to mass spectrometry, a peak based on M+ was found at m/e 680. A peak based on calbonyl group was observed at 1740 cm$^{-1}$ in infra-red spectrophotometry, as shown in FIG. 5. In nuclear magnetic resonance spectrometry (CDCl$_3$), as shown by the chart in FIG. 6, signals were noted based on methyl and methylene protons of phytosterol at 0.6~2.0 ppm, and —(CH$_2$)— of long chain fatty acid residue at 1.28 ppm. A signal of triplet based on methylene group adjacent carbonyl groups, a signal of multiplet (12 Hz in half width) based on hydrogen of $C_3$ phase and a signal of multiplet based on binyl hydrogen were found at 2.25 ppm, 4.6 ppm and 5.35 ppm, respectively. Then, the material was subjected to alkalic hydrolysis to be classified into an acid and a neutral fractions. The neutral fraction was proved to contain sterol, which comprised β-sitosterol and campesterol. The acid fraction was a mixture of higher fatty acid comprising in substance stearic acid and palmitic acid, which was determined by means of methylation and gas chromatography.

In conclusion, the said Y component was identified as a mixture of long chain fatty acid esters of phytosterol. A part of this material was identical to β-sitosterol derivative mentioned by Kuksis et al in "Journal of Organic Chemistry", vol. 25, page 1209; in 1960.

Test 6

In this test yield of stanol ferulic acid derivative and phytosterol fatty acid ester from the whole seed, coix seed, bran and hulls of Job's tears was compared to each other.

The whole seed of Job's tears was ground in a known manner, threshed and purified, and thus separated into hulls, bran and coix seed. Among 100 parts of the whole seed, 33 parts of the hulls, 15 parts of the bran and 52 parts of the coix seed were obtained. To these four starting materials were respectively added n-hexane and ethyl acetate each in a triple quantity thereof, and the solution was agitated at 15°~20° C. for 5 hours, to thereby effect extraction. After the respective extracting solvents had been removed, oily components were obtained. The weight ratios of the respectively oily components with the starting materials are shown in the following Table III, which shows the fact that the effective components comprising ferulyl stanol derivative and phytosterol fatty acid ester are both included in the bran of Job's tears seed.

TABLE III

| starting material | oily component extracted with n-hexane | oily component extracted with ethyl acetate | yield per 1 g oily component (g) | |
|---|---|---|---|---|
| | | | ferulyl stanol derivative | phytosterol fatty acid ester |
| whole | 9.3 | 12.2 | 0.0011 | 0.0201 |
| hull | 0.12 | 0.18 | little | little |
| bran | 16.0 | 25.1 | 0.0011 | 0.0145 |
| coix seed | 5.4 | 7.3 | little | little |

Test 7

This test was carried out to determine fractions containing the effective components comprising ferulyl stanol derivative and phytosterol fatty acid ester, by means of silical gel chromatography.

(1) Preparation of Test Samples

According to the method described later in Example 3, 1,250 g of an oily fraction was extracted from 5 kg of Job's tears seed bran with ethyl acetate and ethanol.

300 g of oily fraction was subjected to column chromatography using 5 kg of silica gel, wherein the eluent was at first n-hexane and then mixtures of n-hexane and ethyl acetate in mixing ratios being varied to gradually increase the proportion of ethyl acetate. The eluates were 4.352 g of F-I component eluted with a mixture of n-hexane and ethyl acetate in a mixing ratio of 100:1, 283 g of F-II component with an eluent of a 20:1 mixture and 8.756 g of F-III component with ethyl acetate alone. F-I component was purified by column chromatography using 250 g silica gel and a mixed eluent of n-hexane and ethyl acetate in a ratio of 100:1. F-II component was further subjected to alumina column chromatography and eluted with a 20:1 mixture of n-hexane and ethyl acetate to obtain 128 mg of F-II-1 component, 1.284 g of F-II-2 component, 210 mg of F-II-3 component, 210 mg of F-II-4 component and 55 mg of F-II-5 component. Thus, seven specimens were prepared.

(2) Test Method for Physiological Activities

These seven specimens were dissolved into 0.2 ml of a soy bean oil to prepare various oil solutions, which were orally given once a day to respective groups each having 10 golden hamsters in the age of 5~8 weeks. The amounts of the components respectively contained in such oil solutions were made different to be 0.2 mg and 0.5 mg. During the administration for 3 weeks with such oil solutions, the sex periods and the number of naturally produced ova were observed, the results of which were compared with those of reference group which had been treated with 0.2 mg of soy bean oil containing no sample component.

(3) Results

The results with respect to the natural ovulation are shown in table IV.

TABLE IV

| component added | amount of component added | |
|---|---|---|
| | 0.2 mg | 0.5 mg |
| (reference) | 12 | 12 |
| F-I | 18 | 15 |
| F-II-1 | 12 | 10 |
| F-II-2 | 11 | 10 |
| F-II-3 | 12 | 12 |
| F-II-4 | 18 | 13 |
| F-II-5 | 12 | 11 |
| F-III | 11 | 12 |

The sex periods were 4 days for all groups including the reference and there could be found no disturbing effect on the sex period. It will be quite obvious that F-I and F-II-4 components have significant ovulation-induce effect. These components were identified in a known manner to determine that F-I component was phytosterol fatty acid ester and F-II-4 component was ferulyl stanol derivative.

Test 8

This test was performed to determine effective dosage of stanol ferulic acid derivative, an effective ovulation-inducing component of the fertility drug according to the invention.

(1) Preparation of Test Sample

X component was prepared in the same manner as in Example 3, described later, and used as a test sample. X component was a 9:1 mixture of trans-ferulylstigmastanol and trans-ferulylcampestanol.

(2) Test Method

The test was carried out in the same manner as in Test 7, except the amounts of the component added in the soy bean oil were 0.1 mg, 0.2 mg and 1.0 mg once a day, respectively.

(3) Results (3-1) Sex Period

TABLE V

| amount of component added | sex period (day) |
|---|---|
| (reference) | 4 |
| 0.1 mg | 4 |
| 0.2 mg | 4 |
| 1.0 mg | 4 |

As shown from Table V, each group showed regular sex period.

(3-2) Number of Natural Ovulation

TABLE VI

| amount of component added | number of natural ovulation |
|---|---|
| (reference) | 11 ± 1 |
| 0.1 mg | 16 ± 1 ※ |
| 0.2 mg | 18 ± 2 ※ |
| 1.0 mg | 13 ± 2 |

Note:
The mark ※ shows a significance at a significance level of 1%.

As shown from Table VI, the groups to which 0.1 mg and 0.2 mg of the effective components were given show significance with P<0.01 with respect to the reference group.

As the average body weight of a hamster used in this test was 150 g and the body weight of an adult is supposed to be 60 kg, the effective dosage to an adult is proved to be 40~80 mg once a day.

Test 9

This test was performed to determine effective dosage of phytosterol fatty acid ester, another effective ovulation-inducing component of the feritility drug according to the invention.

(1) Preparation of Test Sample

Y component was prepared in the same manner as in Example 3, described later, and used as a test sample.

(2) Test Method

The test was carried out in the same manner as in Test 7, except the amounts of the component added in the soy bean oil were 0.1 mg, 0.02 mg and 1.0 mg once a day, respectively.

(3) Results (3-1) Sex Period

TABLE VII

| amount of component added | sex period (day) |
|---|---|
| (reference) | 4 |
| 0.1 mg | 4 |
| 0.2 mg | 4 |
| 1.0 mg | 4 |

It will be quite obvious from Table VII that each group showed regular sex period.

(3-2) Number of Natural Ovulation

TABLE VIII

| amount of component added | number of natural ovulation |
|---|---|
| (reference) | 12 ± 2 |
| 0.1 mg | 16 ± 1 ※ |
| 0.2 mg | 18 ± 2 ※ |
| 1.0 mg | 15 ± 1 |

Note:
The mark ※ shows a significance at a significance level of 1%.

As shown from Table VIII, the groups to which 0.1 mg and 0.2 mg of the effective components were given show significance with P<0.01 with respect to the reference group.

As the average body weight of a hamster used in this test was 150 g and the body weight of an adult is supposed to be 60 kg, the effective dosage to an adult is proved to be 40~80 mg once a day.

Ferulyl phytostanol derivative, one of the effective components having ovulation-inducing effect, may be prepared not only by extraction from Job's tears seed as described before, but also by synthetic method. Such a synthetic method of production of ferulyl phytostanol derivative is characterized by successive steps of acetylating ferulic acid with a mixture of pyridine and acetic anhydride, treating the acetylated ferulic acid with thionyl chloride to form an acid chloride, reacting in the presence of pyridine the acid chloride and phytostanol to prepare phytostanol compound, dissolving the phytostanol compound into a mixture of methanol and chloroform, and adding sodium boron hydride to a resulting solution, with stirring, to thereby deacetylate the phytostanol compound.

The respective steps will be described in detail as follows.

(A) Acetylation

Ferulic acid (4-hydroxy-3-methoxycinnamic acid) is dissolved into a liquid mixture of pyridine and acetic anhydride (mixing ratio of 3:1) in a concentration of 10~15 wt.%. After reflux for 4~5 hours the solvent is distilled to prepare acetylated ferulic acid.

(B) Formation of Acid Chloride

The acetylated ferulic acid is dissolved into chloroform anhydride in a concentration of 10~15 wt.%. Thionyl chloride (SOCl$_2$) is added to the solution in a proportion of 1.5 moles per 1 g acetylated ferulic acid to effect the reaction thereof at 20°~30° C. for 5~6 hours. Then, the solvent is distilled in pressure reduced conditions to prepare acid chloride.

(R: —CH₃ or —C₂H₅)

ice-cooled condition to effect the reaction at 20°~30° C. for 2~3 hours, and the solvent is distilled and removed.

(C) Reaction with Phytostanol

The acid chloride thus prepared is dissolved into pyridine in a concentration of 10~15 wt.% to prepare a first solution, and an equivalent of phytostanol is dissolved into pyridine to prepare a second solution. The first solution is dropped into the second solution in an

(D) Deacetylation

The reactant thus obtained in the step (C) is dissolved into a liquid mixture of chloroform and methyl alcohol (mixing ratio of 1:1) in a concentration of 3~5 wt.%. While this solution is being agitated in an ice-cooled condition, sodium borohydride in a quantity of double equivalent is added thereto by degree. After the foaming has ceased the solution is allowed to stand at 20°~25° C. for 1~1.5 hours, a small quantity of water is added and then the solvent is evaporated in pressure reduced conditions. Thus, ferulyl phytostanol derivative is prepared.

(R: —CH₃ or —C₂H₅)

Ferulyl phytostanol thus prepared by the successive steps (A) to (D) may be further purified by silica gel column chromatography and then recrystalized with methyl alcohol, thereby producing the same in a pure state. Alternatively, the purification may be carried out each time the intermediate product is formed in each step.

The followings are exemplifying tests for the method of producing ferulyl phytostanol derivative according to the invention.

Test 10

This test was carried out to examine physical and chemical characteristics of the intermediate product formed by the acetylation step (A).

(1) Preparation of Test Sample

Test sample was prepared in the same manner as the acetylation step in Example 6, described later. The acetylated product was subjected to silica gel column chromatography whereby a fraction eluted with acetone was obtained, from which acetone was evaporated to prepare a purified test sample.

(2) Test Method

The test sample was put into tests for melting point, mass spectrometry, infra-red spectrophotometry (KBr method) and nuclear magnetic resonance spectrometry (CD₃OD+CDCl₃) in known manner.

(3) Results

The test results were as follows.

mp. 195°~196° C., FD-MS m/e; 236 (M+) IRν(KBr) Cm⁻¹; 3500 (COOH), 1760, 1690 (>C=O), 1630 (—COOH=CH—), NMR (CD₃OD+CDCl₃), ppm: 2.32 (3H, S, COCH₃), 3.82 (3H, S, OCH₃), 6.32 (1H, d, J=16 Hz, —COCH=CH—), 7.07 (3H, m, aromatic ring), 7.60 (1H, d, J=16 Hz, —COCH=CH—).

Consequently, the test sample was identified as 4-acetylferulic acid (4-acetoxy-3-methoxycinnamic acid).

Test 11

This test was carried out to observe physical and chemical characteristics of the intermediate product formed by the reaction of acetylated ferulic acid chloride and stigmastanol.

(1) Preparation of Test Sample

Test sample was prepared in the same manner as the step of formation of acid chloride in Example 6, described later. The acid chloride compound thus prepared was subjected to silica gel column chromatography with a mixed eluent of n-hexane and ethyl acetate ester (mixing ratio of 20:1). The eluate was recrystalized with methyl alcohol to prepare a purified test sample.

(2) Test Method

The tests applied to the sample were the same as in Test 10. The elementary analysis was carried out in a known manner.

(3) Results

A melting point was 156° C. The results of the elementary analysis were C: 77.80 and H: 9.89, which are in conformaty to the calculated values of C: 77.60 and H: 9.78 according to the molecular formula of $C_{41}H_{62}O_5$ of 4-acetylferulylstigmastanol.

The results of mass spectrometry, infra-red spectrophotometry and nuclear magnetic resonance spectrometry were as follows.

FD-MS m/e; 634 (M+), IR$\nu$ (KBr): 1770,1710 (>C=O), 1640 (—COOH=CH—), 1600,1510 (benzene ring), 1180,1080 (—C—O—C—), NMR (CDCl$_3$), ppm: 0.6~2.0 (—CH$_3$, —CH$_2$—), 2.32 (3H, S, COCH$_3$), 3.84 (3H, S, OCH$_3$), 4.70 (1H, m, —O—CH<), 6.32 (1H, d, J=16 Hz, —COCH=CH—), 7.07 (3H, m, aromatic ring), 7.60 (1H, d, J=16 Hz, —COCH=CH—).

In accordance with these results the test sample was identified as 4-acetylferulylstigmastanol.

Test 12

This test was performed to test physical and chemical characteristics of the final product prepared by the method of the invention.

(1) Preparation of Test Sample

Test Sample was prepared and purified by the same method as in Example 6.

(2) Test Method

The same tests were applied as in Test 11.

(3) Results

A melting point was 152° C. The results of the elementary analysis were C: 79.17 and H: 9.86, which are in good agreement with those of C: 79.05 and H: 10.14 calculated according to the molecular formula of $C_{39}H_{60}O_4$.

The results of mass spectrometry, infra-red spectrophotometry and nuclear magnetic resonance spectrometry were as follows.

FD-MS m/e; 592 (M+), IR$\nu$ (KBr); Cm$^{-1}$: 3200-3500 (—OH), 1710 (—CO), 1640 (—COOH=CH—), 1600,1520 (benzene ring), 1180,1080 (—C—O—C—), NMR (CDCl$_3$), ppm: 0.6~2.0 (—CH$_3$, CH$_2$ of sterol<), 3.88 (3H, S, —OCH$_3$), 4.72 (1H, m, —O—CH<), 5.96 (1H, S, —OH), 6.22 (1H, d, J=16 Hz, —COCH=CH—), 6.98 (3H, m, aromatic ring), 7.55 (1H, d, J=16 Hz, —COCH=CH—).

In conclusion, the final product was identified as trans-ferulyl stigmastanol.

For better understanding of the invention some preferred examples thereof will be given hereunder.

EXAMPLE 1

5 kg powder of Job's tears prepared by grinding the whole seed thereof was subjected to extraction with 15 l n-hexane at a temperature of 20° C. and the solvent was evaporated at a temperature below 40° C. under reduced pressure, thereby obtaining about 450 g of a yellow, oily material at extractability of about 9%. This extractant was then purified by silica gel chromatography with n-hexane. The purified extractant was added to basic feed to prepare fodder which was given to a group having 10 golden hamsters in the age of 5~8 weeks. The quantities of the fodder given to a golden hamster and the purified n-hexane extractant contained therein were determined 19 g and 171 mg a day, respectively. While the test animals were fed for 3 weeks the sex periods were observed, and thereafter they were slaughtered to measure the number of naturally produced ova and observe the state of the ovaria. For reference, an equivalent quantity of the basic fodder not containing the purified n-hexane extractant, was given to another group also having ten golden hamsters, to which the same tests were applied.

The test results are shown in Table IX, from which it is confirmed that the oil-soluble fraction of the whole seed of Job's tears has a favorable effect on natural ovulation and formation of corpora lutea, without disturbing sex periods.

TABLE IX

| test group | comparison of sex period | | number of natural ovulation | dissection test | |
|---|---|---|---|---|---|
| | sex period | remarks | | weight of ovary (mg) | state of ovary |
| this invention | 4.5 days | regular | 16 ± 2 ※ | 19.25 ± 1.66 | (++) |
| reference | 4 days | regular | 12 ± 2 | 18.08 ± 0.16 | (±) |

Note:
The representation of sex period and the marks identified above show the same meanings as in Table I.

EXAMPLE 2

In Example 1 was used the whole seed of Job's tears but in this example 500 g bran of Job's tears was used, and by extraction with 1.5 l n-hexane at 20° C. was obtained about 80 g of a yellow oily material at extractability of about 16%. This material was purified by silica gel chromatography with n-hexane and the solvent was evaporated at 40° C. under redcuced pressure, thus preparing about 72 g of a purified extractant. This purified extractant was given to a group of ten golden hamsters in a proportion of 1.5 mg a day per 1 g of the body weight of a golden hamster, and the same tests were put into practice as in Example 1, results of which are shown in Table X. As shown, the oil-soluble fraction of the bran of Job's tears seed will promote natural ovulation without disturbing the sex period and bring a significant effect on formation of corpora lutea.

TABLE X

| test group | comparison of sex period | | number of natural ovulation | dissection test | |
|---|---|---|---|---|---|
| | sex period | remarks | | weight of ovary (mg) | state of ovary |
| this invention | 4 days | regular | 18 ± 2 ※ | 19.48 ± 1.51 | (++) |
| reference | 4 days | regular | 12 ± 2 | 17.92 ± 0.23 | (±) |

Note:
The representation of sex period and the marks identified above show the same meanings as in Table I.

EXAMPLE 3

50 kg of Job's tears seed was threshed and purified in known manner to prepare about 6.5 kg bran, among which 5 kg bran was subjected to extraction with 5 kg ethyl acetate at 20° C. for 5 hours while being agitated. This extraction procedure was repeated three times to obtain a first extractant. To 4 kg of the residue was added 10 kg ethanol, and the reaction solution was agitated at 20° C. for 5 hours. This second extraction procedure was repeated twice and then the collected extracs were filtered to remove insoluble fractions. From the ethanol-soluble fraction thus obtained was evaporated ethanol in a known manner. To 120 g of the resulting component was added 360 g ethyl acetate and the solution was agitated at 20° C. for 5 hours, to extract an ethyl acetate soluble fraction, a second extractant.

The first and second extractants were mixed together. Ethyl acetate was evaporated and removed from the extractant mixture to obtain 1,310 g of an oil-and-fat fraction.

A first portion of 500 g of the oil-and-fat fraction was subjected to column chromatography charged with 8 kg silica gel, whereby 450 g eluate was obtained with a mixed eluent of n-hexane and ethyl acetate (mixing ratio of 20:1). This eluate was further introduced to alumina column chromatography (800 g) whereby elution was effected with a mixed eluent of n-hexane and ethyl acetate (mixing ratio of 20:1) and about 540 mg of a fraction showing a spot in ultraviolet rays was obtained by a fraction collector. This component was subjected to reverse phase high performance liquid chromatography utilizing Rp-18 with a mixed eluent of ethyl acetate and methanol (mixing ratio of 5:3), to obtain about 450 mg of a component having a U V absorption. This component was further subjected to column chromatograpy using 50 g of silica gel with a mixed eluent of n-hexane and ethyl acetate (mixing ratio of 20:1), to elute about 330 mg of a component (X component) having a U V absorption. X component was put into the same tests as in Test 7 so that it was proved to have ovulation-inducing effect.

On the other hand, another portion of 500 g of the oil-and-fat fraction was subjected to column chromatograph using 8 kg silica gel, with a mixed eluent of n-hexane and ethyl acetate (mixing ratio of 100:0.5), then an eluate (Y component) was obtained in a quantity of about 6.87 g. Y component was also submitted to the same tests as in Test 7 and its ovulation-inducing effect was observed.

EXAMPLE 4

To 3 kg of Job's tears bran was added 3 kg ethyl acetate and the solution was agitated at 17° C. for 8 hours for effecting extraction. This extraction procedure was repeated four times and extractants obtained in respective extraction were combined. Thus, an ethyl acetate extractant was prepared. To 2.2 kg of the residue was added 8 kg ethanol and the mixture was agitated at 17° C. for 8 hours. The extract thus obtained was filtered to remove insoluble components. By evaporating ethanol from the ethanol-soluble fraction in a known manner, an extractant with ethanol was obtained in a quantity of 65 g. To this extractant was added 260 g ethyl acetate, and the solution was agitated at 17° C. for 8 hours, to extract an ethyl acetate soluble extractant. These two ethyl acetate extractants were combined, from which ethyl acetate was evaporated to obtain 790 g of an oil-and-fat fraction.

A first portion of 300 g of the oil-and-fat fraction was subjected to column chromatography using 5 kg silica gel, with a mixed eluent of n-hexane and ethyl acetate (a mixing ratio of 30:1), to obtain an eluate in a quantity of 269 g. This eluate was subjected to alumina column chromatograpy (500 g), thereby obtaining 330 mg of a fraction having a spot in ultraviolet rays. This fraction was subjected to reverse phase high performance liquid chromatography utilizing Rp-18, thereby eluting with a mixed eluent of ethyl acetate and methanol (a mixing ratio of 5:3) to obtain about 248 mg of a component having a U V absorption. This component was further subjected to column chromatography using 30 g silica gel with a mixed eluent of n-hexane and ethyl acetate (a mixing ratio of 30:1) to obtain about 190 mg of a fraction having a U V absorption. This fraction was submitted to tests in the same manner as in Test 7 so that it was proved to have ovulation-inducing effect.

On the other hand, the other portion of 300 g of the oil-and-fat fraction was subjected to column chromatography using 5 kg silica gel with a mixed eluent of n-hexane and ethyl acetate (a mixing ratio of 100:1) to obtain 4.352 g of an eluate. This eluate was tested in the same manner as in Test 7 to find its significant ovulation-inducing effect.

EXAMPLE 5

The procedure in Example 1 was repeated several times to obtain 40 g of X and Y components, respectively, to which 150 g of middle-chain fatty acid triglycerol on the market was added to make 1,000 soft capsule medicines therefrom, respectively. A soft capsule medicine made from X component contained 40 mg of the effective component (that is, a 9:1 mixture of trans-ferulylstigmastanol and trans-ferulylcampestanol) and a soft capsule medicine made from Y component contained 80 mg of the effective component (that is, phytosterol long-chain fatty acid esters in a mixed state).

EXAMPLE 6

According to the following steps trans-ferulyl stigmastanol was synthetically manufactured.

(1) Acetylation 1.0 g of ferulic acid (Tokyo Kasei Kougyo K.K., corresponding to 5.15 m moles) was dissolved into 8 ml of a liquid mixture of pyridine and acetic anhydride in a mixing ratio of 3:1, and after reflux for 4 hours the solvent was evaporated.

(2) Formation of Acid Chloride 1.0 g of the acetylated ferulic acid (4.24 m mol) was dissolved into 10 ml chloroform anhydride and 0.46 ml (6.36 m moles) of thionyl chloride (Wako Jun'yaku K.K.) was added to the solution, to effect the reaction thereof at 25° C. for 5 hours, and then the solvent was evaporated under reduced pressure.

(3) Reaction with Phytostanol

The acid chloride compound thus obtained was dissolved into 10 ml pyridine anhydride and the resultant was dropped in an ice-cooled condition into 10 ml of another pyridine solution prepared by dissolving thereto 1.77 g (4.24 m moles) of stigmastanol (Aldrich Chemical Co.,). After the solution had been allowed to stand at room temperature for 2 hours, the solvent was evaporated. The remaining residue was subjected to a silica gel column, and the column was eluted with a mixed eluent of n-hexane and ethyl acetate (a mixing ratio of 20:1). Thus, a reactant was obtained in a quantity of 1.65 g.

(4) Deacetylation and Purification 1.6 g of the reactant was dissolved into 48 ml of a liquid mixture of chloroform and methyl alcohol (a mixing ratio of 1:1), and 480 mg (12.7 m moles) of sodium borohydride (Wako Jun'yaku K.K.) was added thereto little by little. After the foaming had ceased the reaction mixture was allowed to stand for 1 hour, and then 1 ml water was added thereto. The solvent was then removed under reduced pressure.

The reaction product was dissolved into 5.0 ml of chloroform and the solution was led to a column charged with silica gel, which was eluted with a mixture of n-hexane and ethyl acetate (a mixing ratio of 20:1). The eluate was recrystalized with methyl alcohol to obtain 1.23 g (2.08 m moles) of colorless, needle-like crystals, that is transferulylstigmastanol, in 83% yield.

EXAMPLE 7

(1) Acetylation

Acetylation was carried out in the same manner as in Example 6.

(2) Formation of Acid Chloride

Acid chloride was formed in the same manner as in Example 6.

(3) Reaction with Phytostanol

The acid chloride was dissolved into 10 ml pyridine anhydride and the resulting solution was dropped into 10 ml of a separately prepared pyridine solution containing 1.72 g (4.2 m moles) campestanol, in an ice-cooled condition. The solution was concentrated and then led to a silica gel column which was eluted with a mixture of n-hexane and ethyl acetate (a mixing ratio of 20:1), thus obtaining 1.45 g of a reactant.

(4) Deacetylation and Purification 1.4 g (2.25 m moles) of the reactant was dissolved into 42 ml of a liquid mixture of chloroform and methyl alcohol (a ratio of 1:1), and to the solution was added little by little sodium borohydride (Wako Jun'yaku K.K.) in a total quantity of 478 mg (12.6 m moles). The reaction mixture was allowed to stand at room temperature for 1.5 hours after the foaming had ceased. The excessive sodium borohydride was inactivated by adding water and then the solvent was evaporated under reduced pressure.

The resulting residue was dissolved into 4.5 ml chloroform and the solution was subjected to a silica gel column which was eluted with a mixture of n-hexane and ethyl acetate (a mixing ratio of 20:1) and recrystalized with methyl alcohol. Thus, trans-ferulylcampestanol in a quantity of 1.15 g (1.73 m moles) was obtained in 77% yield.

Although this invention has been described in conjunction with specific exemplifying tests and preferred embodiments thereof, it is to be understood that many variations may be made without departing from the spirits and scopes thereof as defined in the appended claims.

What we claim is:

1. A method for producing a ferulyl stanol derivative, comprising:
    (a) acetylating ferulic acid with a mixture of pyridine and acetic anhydride to prepare an acetylated ferulic acid,
    (b) treating said acetylated ferulic acid with thionyl chloride to form an acid chloride,
    (c) reacting said acid chloride with phytostanol in the presence of pyridine to form a phytostanol compound
    (d) dissolving said phytosterol compound into a liquid mixture of methanol and chloroform to prepare a solution, and
    (e) adding to said solution sodium borohydride, with stirring, to thereby deacetylate said phytosterol compound.

2. The method according to claim 1, wherein said phytostanol comprises stigmastanol, campestanol or a mixture thereof.

* * * * *